(12) United States Patent
Kochamba

(10) Patent No.: US 6,896,666 B2
(45) Date of Patent: May 24, 2005

(54) CUTANEOUS INJECTION DELIVERY UNDER SUCTION

(75) Inventor: Gary Steven Kochamba, Studio City, CA (US)

(73) Assignee: Kochamba Family Trust, Studio City, CA (US)

( * ) Notice: Subject to any disclaimer, the term of this patent is extended or adjusted under 35 U.S.C. 154(b) by 169 days.

(21) Appl. No.: 10/290,819

(22) Filed: Nov. 8, 2002

(65) Prior Publication Data

US 2004/0092875 A1 May 13, 2004

(51) Int. Cl.$^7$ .............................................. A61M 37/00
(52) U.S. Cl. ....................... 604/141; 604/144; 604/146; 604/147; 604/148; 604/201; 604/204
(58) Field of Search ................................. 604/146, 506, 604/513, 115, 131, 132, 134, 136, 139, 141, 143, 144, 147, 148, 156, 157, 200, 201, 204, 212, 187, 194

(56) References Cited

U.S. PATENT DOCUMENTS

| | | | |
|---|---|---|---|
| 3,727,614 A | * | 4/1973 | Kniazuk ...................... 604/115 |
| 4,419,096 A | | 12/1983 | Leeper et al. |
| 4,753,651 A | | 6/1988 | Eckenhoff |
| 4,886,499 A | | 12/1989 | Cirelli et al. |
| 5,226,896 A | | 7/1993 | Harris |
| 5,441,490 A | | 8/1995 | Svedman |
| 5,656,032 A | | 8/1997 | Kriesel et al. |
| 5,658,259 A | | 8/1997 | Pearson et al. |
| 5,693,018 A | | 12/1997 | Kriesel et al. |
| 5,713,866 A | | 2/1998 | Wilmot |
| RE35,986 E | | 12/1998 | Ritson et al. |
| 5,848,990 A | | 12/1998 | Cirelli et al. |
| 5,858,001 A | | 1/1999 | Tsals et al. |
| 5,868,721 A | | 2/1999 | Marinacci et al. |
| 5,906,592 A | | 5/1999 | Kriesel et al. |
| 5,921,962 A | | 7/1999 | Kriesel et al. |
| 5,931,814 A | | 8/1999 | Alex et al. |
| 5,957,891 A | | 9/1999 | Kriesel et al. |
| 6,048,337 A | | 4/2000 | Svedman |
| 6,086,562 A | | 7/2000 | Jacobsen et al. |
| 6,102,896 A | | 8/2000 | Roser |

(Continued)

OTHER PUBLICATIONS http://allergies.about.com/c/ht/00/07/How_Use_EpiPen_AutoInjector0962933067.htm?term, printed Feb. 7, 2003, pp. 1–3.
http://biz.yahoo.com/p/m/mpp.html, printed Feb. 7, 2003, pp. 1–3.
http://www.baxteripump.com/prod/p_over.htm, printed Feb. 7, 2003, pp. 1–3.
http://baxcat.baxter.com/find.rfm?_action=find&_database=Anesthesia&_field=complete& . . . printed Sep. 1, 2002 p. 1.
http://baxcat.baxter.com/find.rfm?_action=find&_database=Infusion&_field=complete&_he . . . printed Sep. 1 2002 2 pages.

Primary Examiner—Nicholas D. Lucchesi
Assistant Examiner—Catherine S. Williams
(74) Attorney, Agent, or Firm—Greenberg Traurig LLP

(57) ABSTRACT

The delivery of a fluid cutaneously is effected by generating a suction force on a surface of a housing. A surface of a cutaneous layer is received under the suction force about which the proximal end of a needle thereby to pierce the cutaneous surface and to effect an injection of fluid. There is generated a suction force to operate the movement of a needle in the housing. The needle is moved under the suction force from the housing thereby to permit piercing a cutaneous layer. The bladder for containing fluid is emptied under the suction into the distal end of the needle and thereby permit the expulsion of fluid through the proximal end of the needle for injection below the cutaneous layer.

52 Claims, 7 Drawing Sheets

U.S. PATENT DOCUMENTS

| | | |
|---|---|---|
| 6,126,637 A | 10/2000 | Kriesel et al. |
| 6,186,982 B1 | 2/2001 | Gross et al. |
| 6,210,369 B1 | 4/2001 | Wilmot et al. |
| 6,251,065 B1 | 6/2001 | Kochamba et al. |
| 6,254,580 B1 | 7/2001 | Svedman |
| 6,258,062 B1 | 7/2001 | Thielen et al. |
| 6,331,172 B1 | 12/2001 | Epstein et al. |
| 6,364,865 B1 | 4/2002 | Lavi et al. |
| 2002/0040208 A1 | 4/2002 | Flaberty et al. |
| 2002/0072733 A1 | 6/2002 | Flaberty |

* cited by examiner

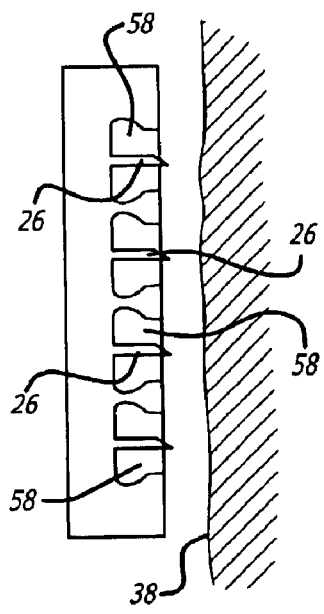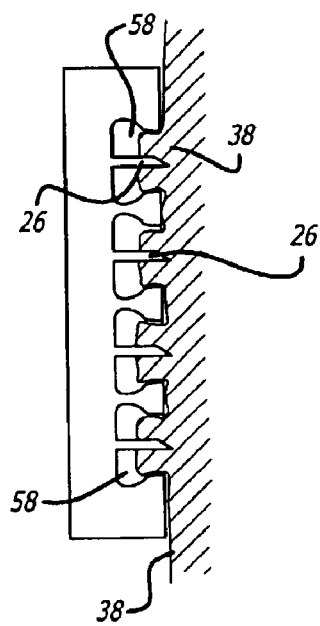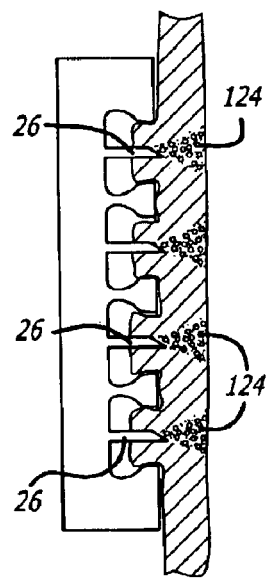
FIG. 7　　　FIG. 8　　　FIG. 9
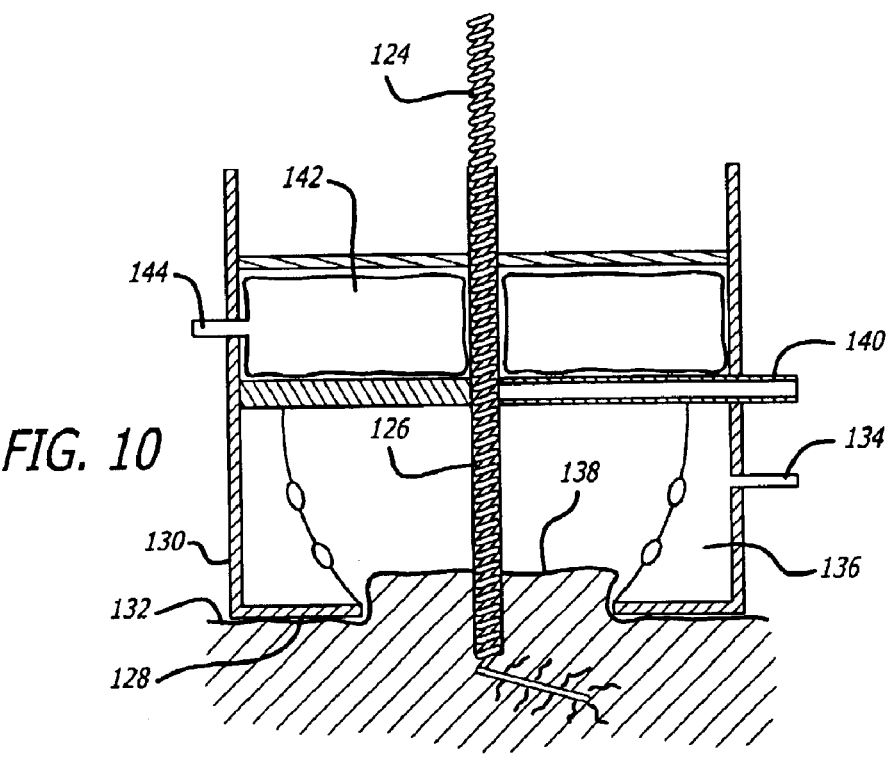
FIG. 10

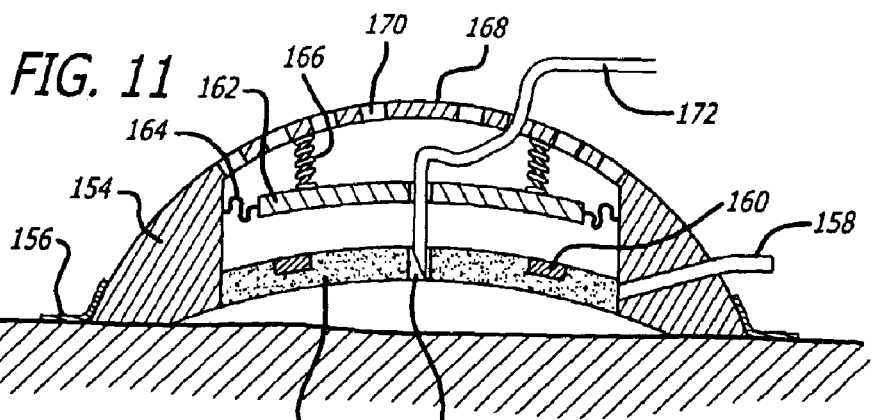
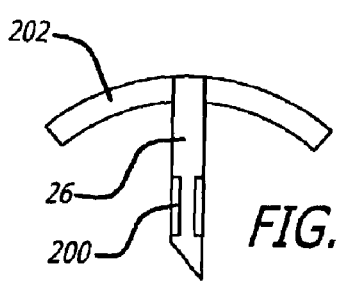
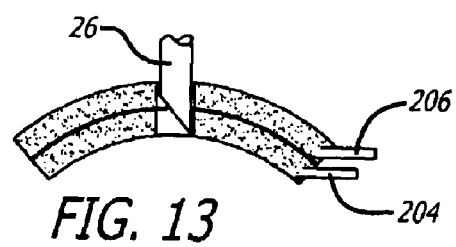
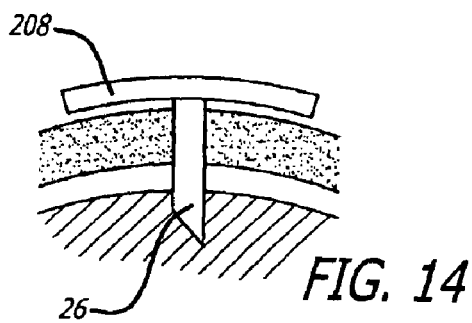
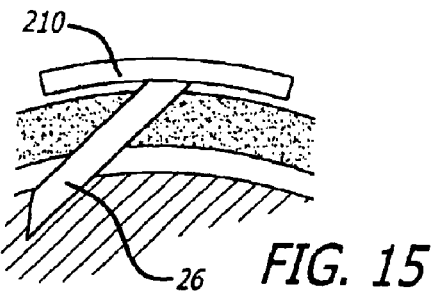
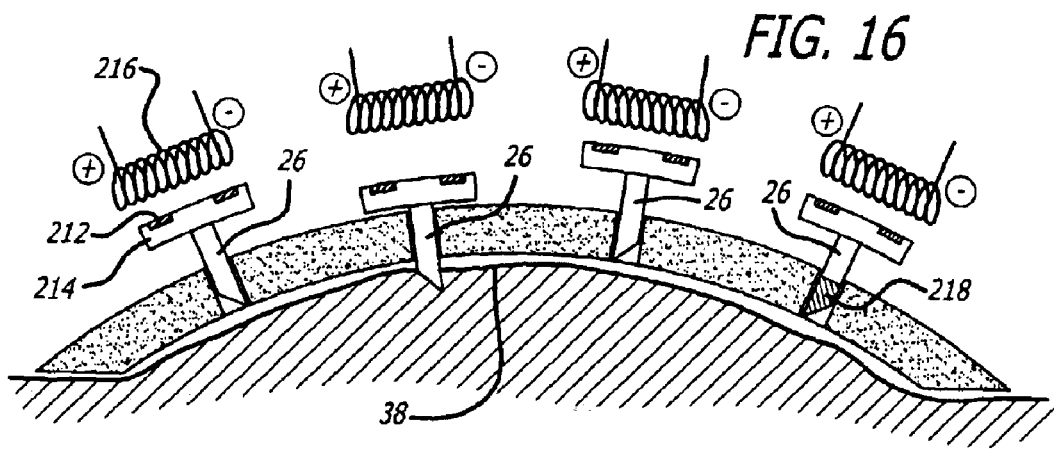

CUTANEOUS INJECTION DELIVERY UNDER SUCTION

BACKGROUND OF THE INVENTION

This invention relates to injection delivery cutaneously or subcutaneously. In particular it relates to a system for stabilizing tissue then facilitating injection of fluids into a body which may be human or animal.

Many systems have been devised for the effective delivery of injectable material such as drugs into a body. These all suffer from one or other drawback.

A conventional method for administration is a hypodermic syringe but this has disadvantages. Particularly, syringes may not be useful for self-administration by patients because of the dangers of embolisms arising from the introduction of air bubbles into the bloodstream, incorrect dosing and accidental infections.

Some syringes are pre-filled, which does correct some disadvantages, but difficulties, however, still arise with the complexity of manipulating the syringes in a smooth or uniform fashion with a single hand. Additionally, some patients have the fear of needles and the sophistication and complexity of mechanical arrangements for activating self-administering syringes generally continues to be a disadvantage. Other disadvantages arise from the system for loading pre-prepared syringes with mechanisms and propellants to activate the syringes throughout the anticipated shelf life of the product.

Needle-less devices are known, but often these require superior dexterity for use and this is also a disadvantage for effecting injections by patients or doctors.

Many other disadvantages can arise from the complexity of different systems.

It is accordingly an object of the present invention to provide an injection delivery system which is capable of delivering preset dosages a drug to a subject, is suitable for self-administration, does not require the conscious insertion of a needle into the skin, is simply constructed for mass production and in different situations can be repetitively used where there are mass dosages provided with the system.

The objects and advantages of the invention are set out further below.

INVENTION SUMMARY

According to the invention there is provided a device, system and method of delivery of fluids by injection to the cutaneous or subcutaneous region of a living body under the effects of a suction or vacuum.

The device includes a housing having a peripheral edge and a needle in the housing for piercing the cutaneous layer. There is a bladder for containing fluid for injection below the cutaneous layer, and an area transversely within the peripheral edge of the housing and through which the proximal end of the needle may be directed. The area is for receiving the surface of the cutaneous layer about which the proximal end of the needle is to pierce to effect an injection of fluid. The area includes a surface, the surface being for receiving the cutaneous layer under action of the suction force. This stabilizes the cutaneous layer prior to and during piercing of the cutaneous layer by the proximal end of the needle.

There is a generator for generating a suction force at the area thereby to urge the cutaneous layer towards the area within the peripheral edge of the housing and thereby provide a stabilizing force to the cutaneous layer. A differential pressure, preferably suction, causes the needle to move through the transverse area and thereby pierce the surface of the cutaneous layer.

The expulsion of fluid from the bladder into the distal end of the needle permits the expulsion of fluid through the proximal end of the needle.

The device includes a mounting for supporting a needle. The suction causes the needle and its mounting to move through the transverse area. The means for providing a suction force causes the movement of the needle mounting and thereby causes the needle to move between a position of repose relatively withdrawn from the transverse area and a position extending through the transverse area.

The device permits the bladder to move under a suction force towards the proximal end of the needle, and thereby permits the distal end to pierce the bladder and permits fluid from the bladder to enter the distal end of the needle and subsequently exit the proximal end of the needle. The bladder is formed in part of elastomeric material whereby the elastomeric material retains a force on the fluid in the bladder.

Applying a further suction to the needle mounting permits movement of the plate a predetermined amount and thereby permits piercing of a sealed chamber in the housing. This causes venting of that suction force which causes the needle to be urged from the position of repose.

The device includes a biasing element means for causing the needle to be urged from the transverse area.

In one preferred form of the invention the transverse surface includes multiple ports through which a suction can be applied to the surface. There can be multiple needles in relative adjacency with each other thereby to permit multiple piercings of the cutaneous layer.

The device includes a suction generating chamber, and an inlet from the suction generating chamber into the housing for transmitting the suction to the housing. At least one secondary needle permits a pressure connection between the inlet for the suction and a ventilation chamber after a predetermined amount of movement of the needle whereby the suction force is vented to the ventilation chamber.

Venting of the suction force firstly permits the needle to be retracted from the exposed position, and thereafter permits the cutaneous layer to move from the transverse area.

In one preferred construction of the device the housing is a cylindrical member with a circular outer edge. The transverse area is an inwardly concavely shaped area within the peripheral outer edge to permit the cutaneous surface to be drawn under suction to form a convex shape against the concave surface. The concave surface has multiple outlets surrounding a location for permitting passage of the needle through the area.

The ventilation chamber is removed from the transverse area. The needle mounting means is located between the transverse area and the bladder, which is located between the needle mounting means and the ventilation chamber.

In another aspect of the invention there is a signaling element or member for indicating the substantial completion of fluid expulsion from the needle. The signaling is selectively an audible signal, the signal being caused by the suction.

Preferably the needle is mounted with a movable plate, the plate having a biasing spring located between a block for holding the needle and the plate. The biasing acts to urge the block and needle from the plate, and the suction acts to urge the block towards the needle plate. The plate is mounted about its periphery with the internal wall of the housing. The mounting includes an elastic diaphragm thereby to permit movement of the plate under action of the biasing and the suction.

In yet a further construction of the device, the bladder is formed with a mounting plate for the needle. One wall of the bladder is the mounting plate, and there is a pierceable member with the mounting plate. Under suction, the plate is drawn towards the distal end of the needle, and the distal end of the needle is permitted to penetrate the pierceable member and enter the bladder. There is a normally sealed wall between the bladder and a ventilation chamber Suction beyond a predetermined level causes the breakage of the sealed wall and thereby the venting of the suction from the transverse area.

The device of the invention preferably has the housing as an elongated structure. The needle is centrally located, and there is sequentially from a proximal end of the housing, firstly the transverse area including a surface through which the needle is adapted to move in an axial direction. Then there is a stabilizing block, one end of which forms the transverse surface. Ports are directed through the block from a side removed from the transverse surface. A guide block is provided for receiving a needle block so that the needle block is movable in the guide block. The guide block has ports to permit suction to pass to an axially movable needle mounting plate. The suction inlet to the housing is located between the guide block and the stabilizing block. The bladder is connected with the needle mounting plate, and the ventilation chamber is located on the opposite side of the bladder.

The device includes one or more secondary needles to permit suction to pass from the suction inlet to the ventilation chamber when the needle plate is moved to a preselected position sufficiently close to the proximal end of the housing. The biasing means urges the needle plate to a position removed from the proximal end of the housing.

A method for delivery of a fluid cutaneously comprises generating a suction force on a surface of a housing thereby to receive under the suction force a surface of a cutaneous layer about which the proximal end of a needle is to pierce to effect an injection of fluid. A suction force operates the movement of a needle in the housing. The needle moves under the suction force from the housing thereby to permit piercing a cutaneous layer. The bladder for containing fluid is emptied into the distal end of the needle and thereby permits the expulsion of fluid through the proximal end of the needle for injection below the cutaneous layer.

More preferably the needle is moved through the transverse area under a suction force. This causes the needle to move between a position of repose relatively withdrawn from the transverse area and a position extending through the transverse area. The bladder is also moved under a suction force towards the distal end of the needle, and this permits the distal end to pierce the bladder and permits fluid from the bladder to enter the distal end of the needle and subsequently exit the proximal end of the needle.

In another aspect of the invention the method for delivery of a fluid subcutaneously comprises applying to the surface including multiple suction points. Multiple piercings are effected through multiple needles in relative adjacency with each other. The bladder moves under a suction force towards the proximal end of the needles. This permits the distal end to pierce the bladder and permits fluid from the bladder to enter the distal end of the needles and subsequently exit the proximal end of the respective needles.

BRIEF DESCRIPTION OF THE DRAWINGS

FIG. 7 is a side view of FIG. 6 without suction;

FIG. 8 is a side view of FIG. 6 with suction;

FIG. 9 is a side view of FIG. 6 during drug delivery;

FIG. 10 is a side view of the interface with an ablation device;

FIG. 11 is a side view of the interface connecting the drug port to a pump;

FIG. 12 is a side view of a needle with a sensor;

FIG. 13 is a side view of the system with porous material and with two suction ports;

FIG. 14 is a side view with the needle orientated at 90°;

FIG. 15 is a side view with the needled orientated at 45°;

FIG. 16 is a side view of needles with electromagnetic mechanisms.

DETAILED DESCRIPTION OF THE PREFERRED EMBODIMENTS

Figure 1:
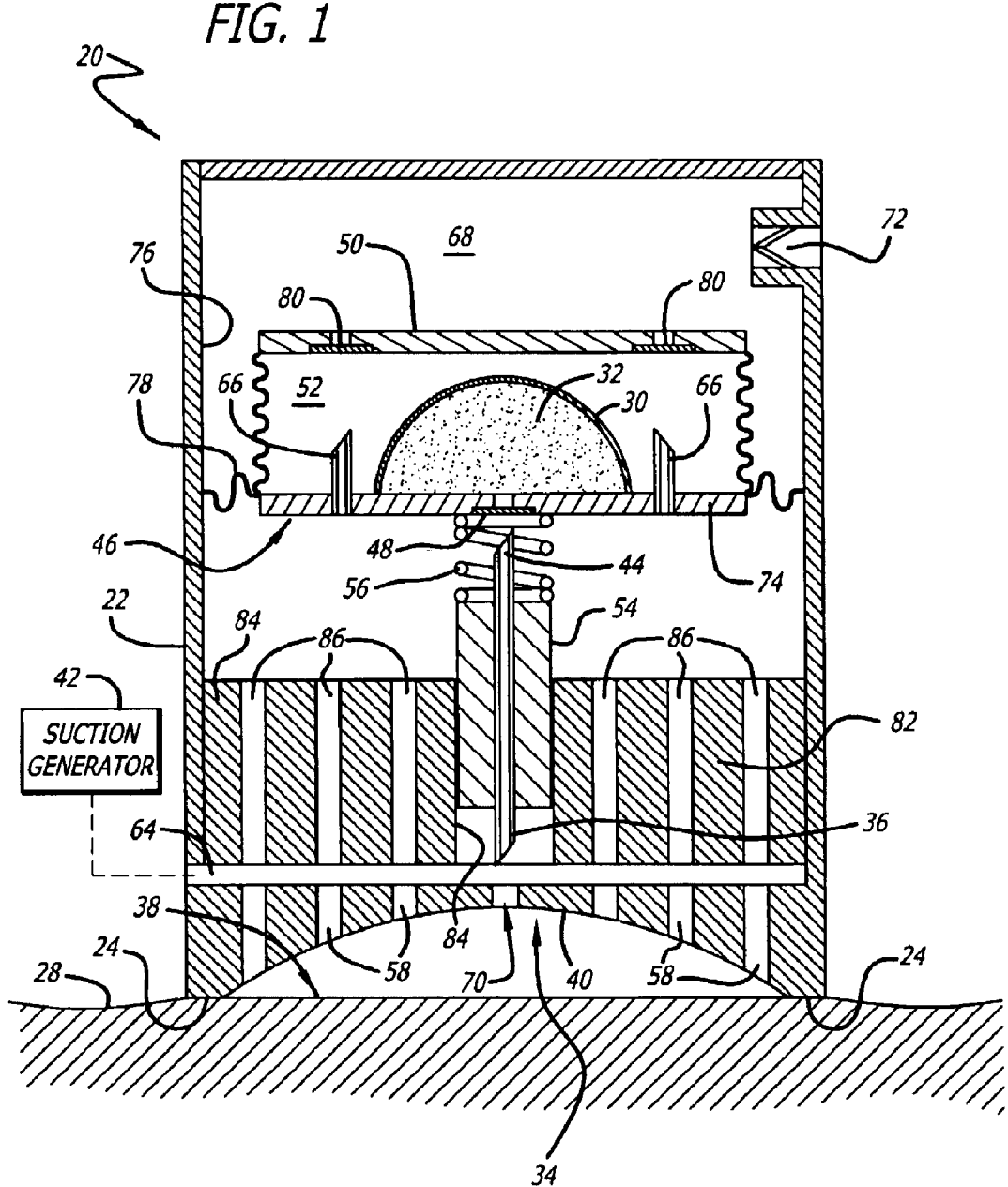
FIG. 1 is a sectional side view of a device according to the invention in a first state.
Figure 2:
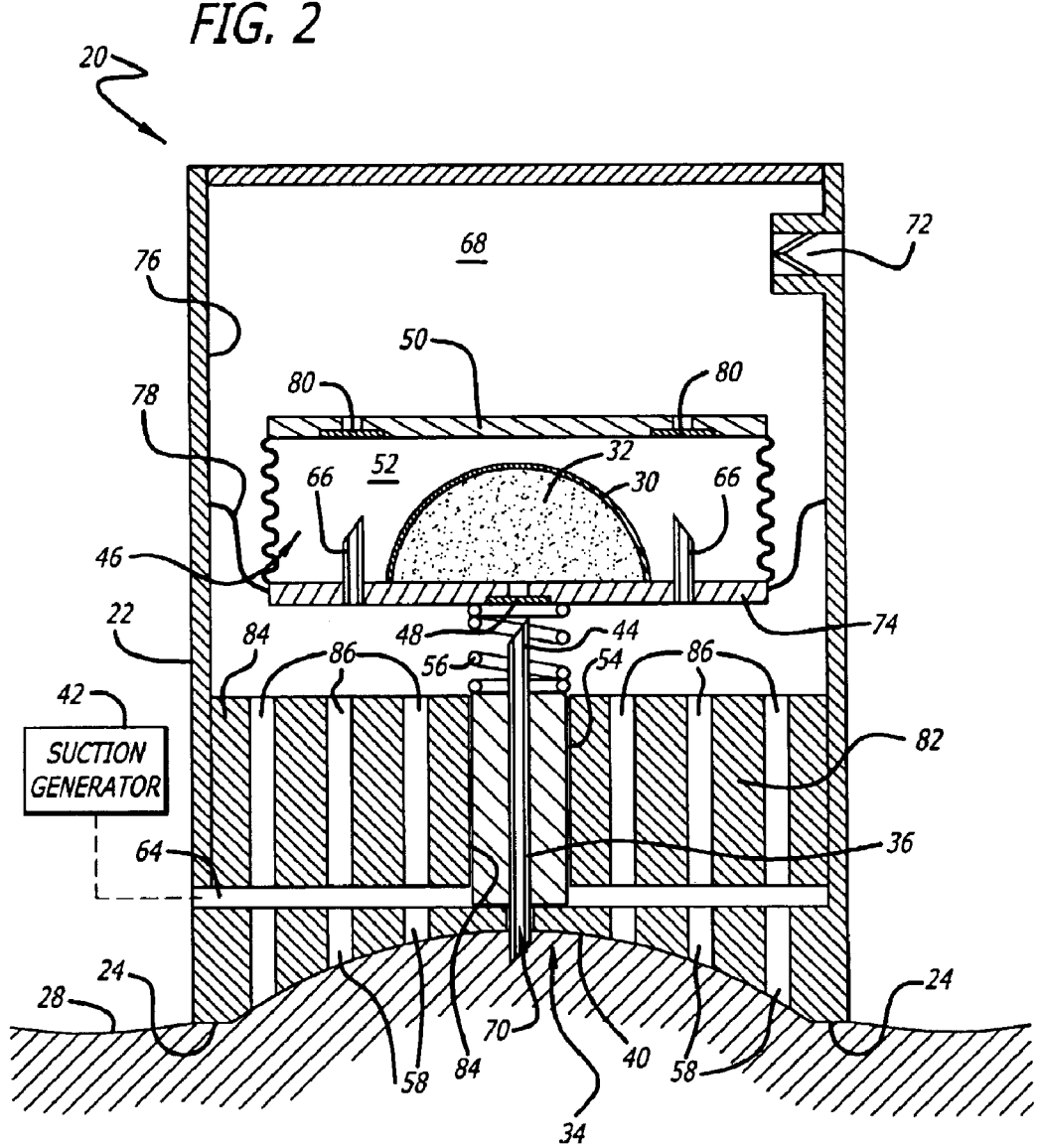
FIG. 2 is a sectional side view of the device in a second state.
Figure 3:
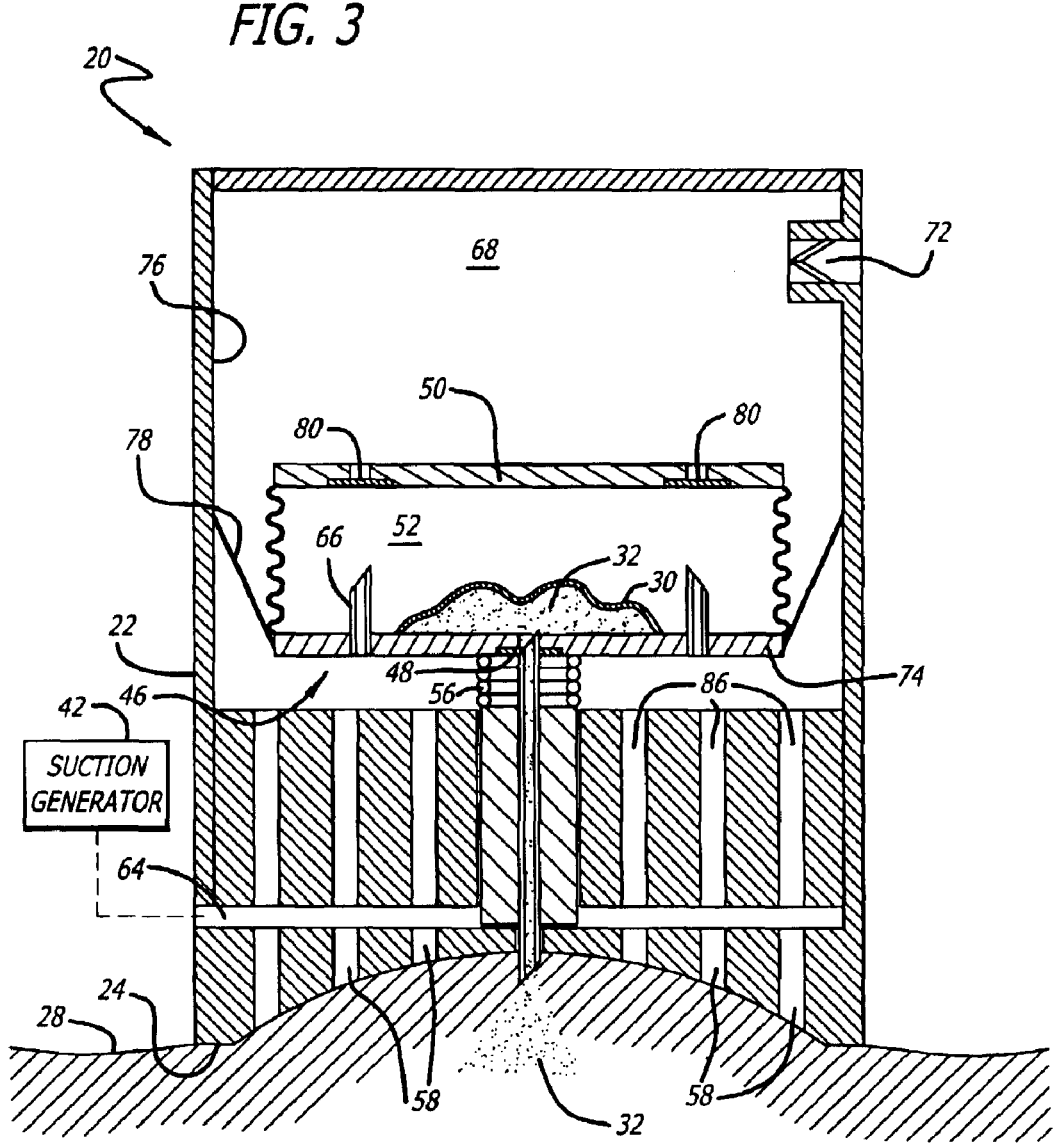
FIG. 3 is a sectional side view of the device in a third state.
Figure 4:
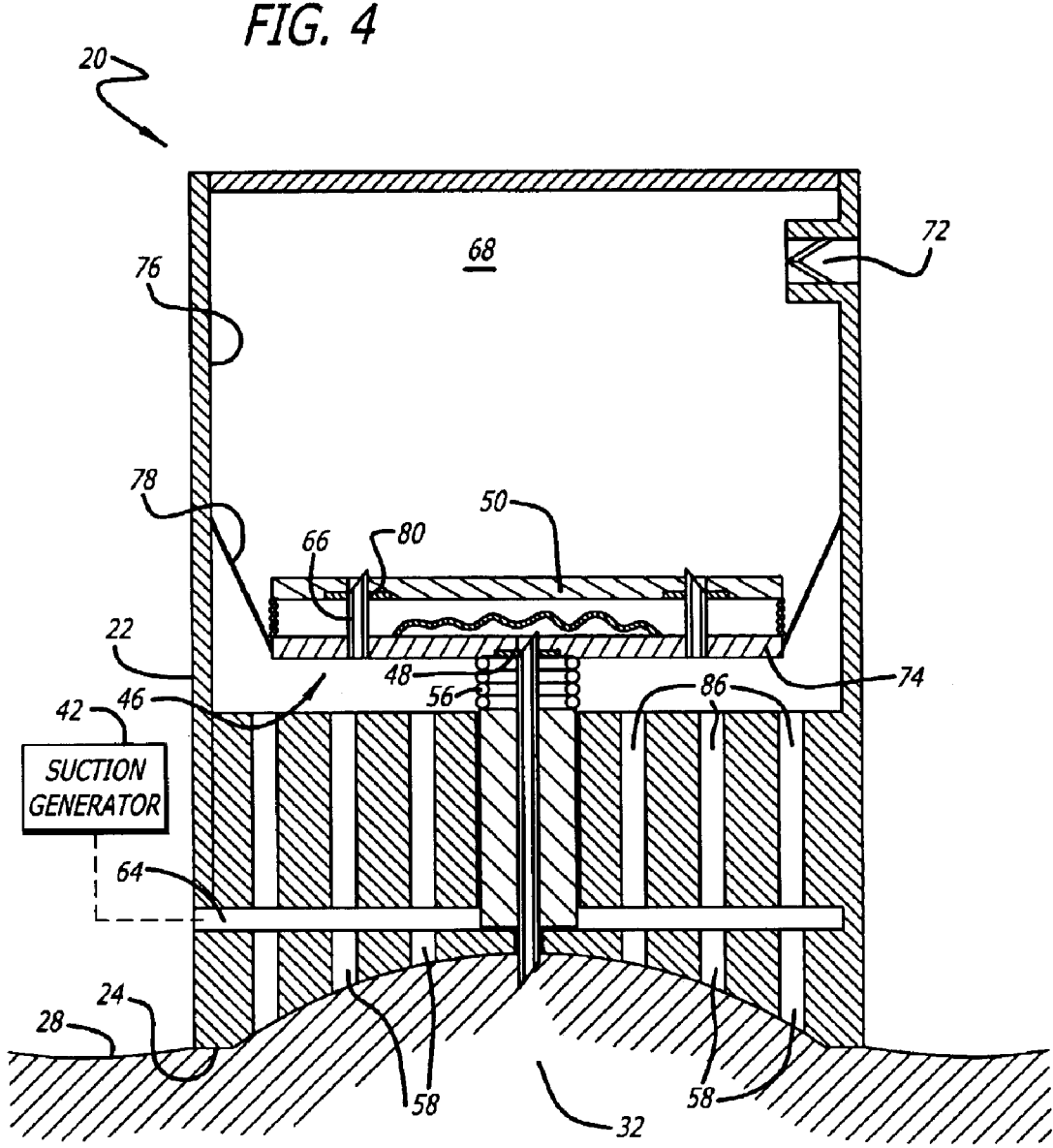
FIG. 4 is a sectional side view of the device in a fourth state.

The invention is described with reference to the accompanying drawings.

A device, system and method is for delivery of fluids by injection to the cutaneous or subcutaneous region of a living body under the effects a suction or vacuum.

The device 20 includes a housing 22 having a peripheral edge 24 and a needle 26 in the housing for piercing the cutaneous layer 28. There is a bladder 30 for containing fluid 32 for injection below the cutaneous layer 28, and an area 34 transversely within peripheral edge 24 of the housing 22 and through which the proximal end 36 of the needle 26 may be directed.

The area 34 is for receiving the surface 38 of the cutaneous layer 28 about which the proximal end 36 of the needle 26 is to pierce to effect an injection of fluid 32. The area 34 includes a surface 40, the surface being for receiving the cutaneous layer 28 under action of the suction force, and thereby stabilize the cutaneous layer prior to and during piercing of the cutaneous layer by the proximal end 36 of the needle 26.

There is a generator device element or means 42 for generating a suction force at the area 34 thereby to urge the cutaneous layer 28 towards the area within the peripheral edge 24 of the housing 22 and thereby provide a stabilizing force to the cutaneous layer 28. The suction causes the needle 26 to move through the transverse area 34 and thereby pierce the surface 38 of the cutaneous layer 28.

The suction effect permits the expulsion of fluid 32 from the bladder 30 into the distal end 48 of the needle 26 and thereby permit the expulsion of fluid 32 through the proximal end 36 of the needle 26.

The device includes a mounting means, member support element or device 40 for supporting a needle, and the suction causes the needle to move through the transverse area 34 to cause the movement of the needle block 54 and thereby cause the needle 26 to move between a position of repose relatively withdrawn from the transverse area 34 and a position extending through the transverse area.

The device permits for and includes a means, element or device for permitting the bladder 30 to move under a suction force towards the proximal end 36 of the needle 26, and thereby permit the distal end 44 to pierce the bladder or an entry 48 to the bladder 30 and permit fluid from inside the bladder to enter the distal end of the needle and subsequently exit the proximal end of the needle.

The bladder 30 is formed in part of elastomeric material whereby the elastomeric material retains a force on the fluid 32 in the bladder 30.

Applying a further suction to the needle mounting plate 74 permits movement of a plate 50 a predetermined amount and thereby permits piercing of a sealed chamber 52 in the housing 46. This causes venting of the suction force which causes the needle 26 and its cylindrical block 54 back to the position of repose.

The device includes a biasing spring 56 for causing the needle 26 to be urged from the transverse area 34. Biasing the needle 26 urges the needle 26 from the transverse area 34. The biasing effect is operable selectively after the needle 26 has been urged into he cutaneous region 28 for a predetermined distance. Further, the biasing action by the spring 56 is selectively effective after the bladder 30 has been substantially emptied.

The transverse surface 40 includes multiple ports 58 through which a suction can be applied to the surface 40. There can be multiple needles 26 in relative adjacency with each other thereby to permit multiple piercings of the cutaneous layer. This embodiment is shown in FIGS. 6 to 9. A suitable port 60 is provided to deliver suction to cause needle movement. Another port 62 is provided to deliver a drug to the needle 26.

The device includes the suction-generating chamber 42, an inlet 64 from the suction-generating chamber 42 into the housing 22 for transmitting the suction to the housing. There is at least one secondary needle or valve 66 for permitting a pressure connection between the inlet 38 for the suction and a ventilation chamber 68, after a predetermined amount of movement of the needle 26 whereby the suction force is vented to the ventilation chamber 68.

Venting of the suction force firstly permits the needle 26 to be retracted from the exposed position, and thereafter permits the cutaneous layer 38 to move from the transverse area 34.

The construction of the device 20 includes the housing 22 which is a cylindrical member with a circular outer edge 24. The transverse area 34 is an inwardly concavely shaped area within the peripheral outer edge 24 to permit the cutaneous surface 38 to be drawn under suction to form a convex shape against the concave surface. The concave surface has multiple outlets 58 surrounding a location 70 for permitting passage of the needle 26 through the area 34.

The ventilation chamber 68 is removed from the transverse area 34. There is the needle mounting means 46 between the transverse area 34 and the bladder 30 is located between the needle 26, mounting means 46, and the ventilation chamber 68.

There is a signaling device, element or whistle means 72, for indicating the substantial completion of fluid expulsion from the needle 26. The signaling is selectively an audible signal, the signal being caused by the suction.

The needle 26 is mounted with a movable plate 74 of the mounting means 46. The plate 74 has the biasing spring 56 located between block 54 for holding the needle 26 and the plate 74. The biasing acts to urge the block 54 and needle 26 from the plate 74, and the suction acts to urge the block 54 towards the needle 26 and plate 74. The plate 74 is mounted about its periphery with the internal wall 76 of the housing. The mounting includes an elastic diaphragm 78 thereby to permit movement of the plate 74 under action of the biasing and the suction.

The bladder 30 is formed with the mounting plate 74 for the needle 26. One wall of the bladder 30 is the mounting plate 74, and there is the pierceable member 48 of the mounting plate 74. Under suction, the plate 74 is drawn towards the distal end 44 of the needle 26, and the distal end 44 of the needle 26 is permitted to penetrate the pierceable member 48 and enter the interior of the bladder 30.

There is a normally sealed wall 50 between the bladder 30 and the ventilation chamber 68, and the suction beyond a predetermined level causes the breakage of the sealed wall 50 at closed ports 80 and thereby the venting of the suction from the transverse area 34.

The housing 22 is an elongated structure. The needle 26 is centrally located, and there is sequentially from a proximal end or edge 24 of the housing, firstly the transverse area 34 including a surface through which the needle 26 is adapted to move in an axial direction. Then there is a stabilizing block 82, one end of which forms the transverse surface 34. Ports are directed through the block from a side removed from the transverse surface 34.

A guide block 84 is provided for receiving a needle block 54 so that the needle block 54 is movable in the guide block 84. The block 84 has ports 86 to permit suction to pass to an axially movable needle mounting plate 74. The suction inlet 64 to the housing 22 is located between the guide block 84 and the stabilizing block 82. The flexible elastic part of the bladder 30 is connected with the needle mounting plate 74, and the ventilation chamber 86 is located on the opposite side of the bladder 30 and also the opposite side of the plate 50.

The device 20 may include one or more secondary needles or valves 66 to permit suction to pass from the suction inlet to the ventilation chamber 68 when the needle plate 74 is moved to a pre-selected position sufficiently close to the proximal end of the housing 22. The biasing means 56 urges the needle plate 74 to a position removed from the proximal end of the housing.

The method for delivery of a fluid cutaneously comprises generating a suction force on a surface area 34, of a housing 22 thereby to receive under the suction force, the surface 38 of the cutaneous layer 28 about which the proximal end of a needle 26 is to pierce to effect an injection of fluid.

The generated suction force operates the movement of the needle 26 in the housing 22. The needle 26 is moved under the suction force from the housing thereby to permit piercing a cutaneous layer.

The bladder 30 for containing fluid is emptied into the distal end 44 of the needle 26 and thereby permits the expulsion of fluid through the proximal end 36 of the needle 26 for injection below the cutaneous layer.

The needle 26 is moved through the transverse area 34 under the suction force and thereby causes the needle 26 to move between a position of repose relatively withdrawn from the transverse area 34 and a position extending through the transverse area 34. Also the bladder 30 is moved under the suction force towards the distal end 44 of the needle 26, and thereby permits the distal end 44 to pierce the bladder cavity and permit fluid from inside the bladder to enter the distal end 44 of the needle 26 and subsequently exit the proximal end 36 of the needle 26.

In another aspect of the method for delivery of a fluid cutaneously, the surface 34 including multiple suction ports 58 is applied to the surface 38. Thereafter, multiple piercings through multiple needles 26 in relative adjacency with each other are applied. The bladder 30 moves under a suction force towards the proximal end of the needles 26, and thereby permits the distal ends to pierce a wall of the bladder 30 and permit fluid from the bladder 30 to enter the distal ends of the needles 26 and subsequently exit the proximal ends of the respective needles 26.

Many variations of the invention are possible. There can be various and additional chambers to those described above. The suction producing chamber 42 or vacuum chamber 42, the ventilation chamber 68 and the fluid or drug bladder 30 do not necessarily need to be in axial relationship with each other in the order that appear in the preferred embodiment. The chambers may be located on the left and right sides of each other in the device.

The suction ports 58 may be on one side of the central axis of the device. This may in some situations cause an imbalanced operation of the suction, with one side of the device experiencing the suction before the other side of the device. Alternative embodiments could balance the suction by utilizing a plurality of suction ports as described, for example two ports, one on each side, or an annular tube either on the outside or the inside of a suction chamber. The tube can have apertures through which the suction could be delivered equally into all parts of the suction chamber. The diameter of each of the openings in the annular tube is optimized with larger openings on one side and smaller on the other to make sure the suction is equal on all sides.

Some advantages of the suction features of the invention include the following. The suction draws the tissue or cutaneous or subcutaneous regions 28 up towards the edge 24 of the housing 22. This stabilizes the tissue prior to entry by the needle 26 into the tissue. The tissue is pulled up and away from other structures that could be damaged by the needle such as bone, tendons and nerves. When the needle 26 enters, the tissue is already stable.

Figure 5:
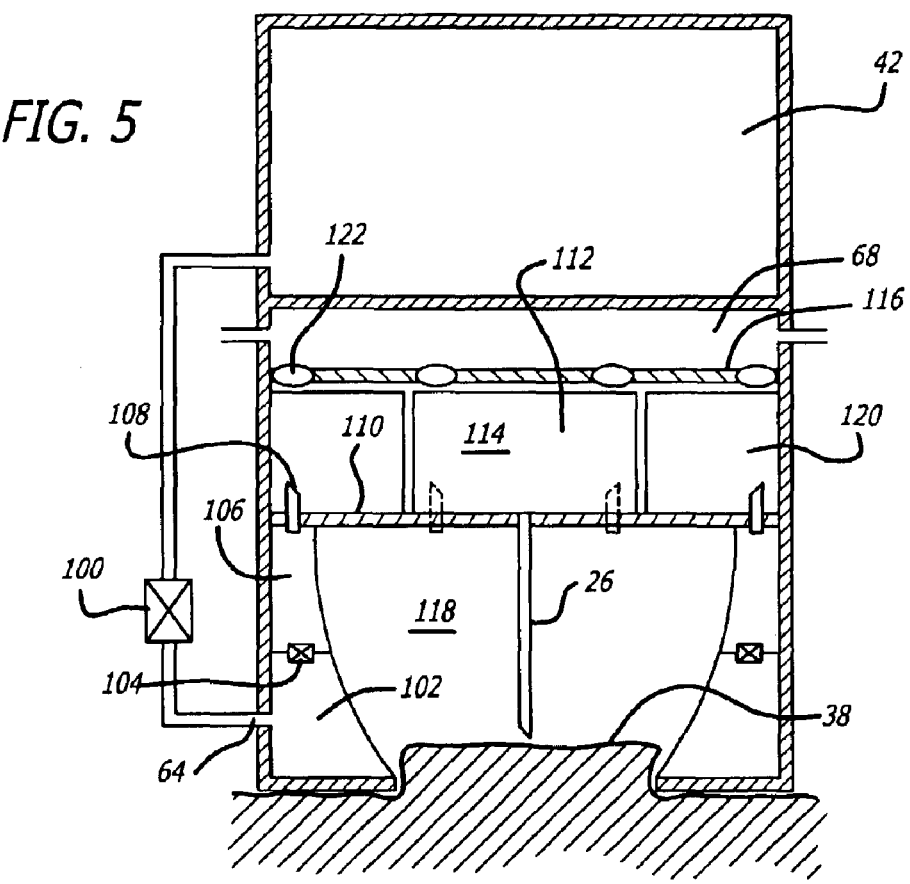
FIG. 5 is a sectional side view of an alternative device.

In FIG. 5 there is shown an embodiment where the suction generator 42 is located above the ventilation chamber 68. The suction chamber is connected through a conduit with a valve 100 to the inlet port 64. The port 64 goes into a bladder 102 which is circumferentially around the inner side of the housing. The bladder 102 is connected through a second valve 104 with a secondary circumferential bladder 106 and there is a needle 108 between a needle plate 110 on which a bladder 112 is mounted to contain fluid 114. A moveable drug plate 116 is located about the drug bladder 112 and forms the base of the ventilating chamber 68. The needle 26 is connected with the drug bladder.

The operation of the system is such that a suction from the suction chamber 42 causes the bladder 102 to compress and then ultimately the bladder 106 to compress. As this happens the needle 26 is drawn downwardly towards the cutaneous layer 38 which is drawn into a chamber-type formation 118. This causes interaction with the proximal end of the needle 26 as the needle plate 110 moves downwardly. The drug plate also moves downwardly and this causes the drug bladder to compress and release fluid 114 through the needle. At a predetermined point the needle 108 pierces the wall of the peripheral bladder 120 and then in turn pierces the drug plate 116 at the membranes 122. This causes a release or ventilation of the suction which would otherwise cause the needle 26 to be drawn downwardly and outwardly. The needle 26 then retracts into the device.

Figure 6:
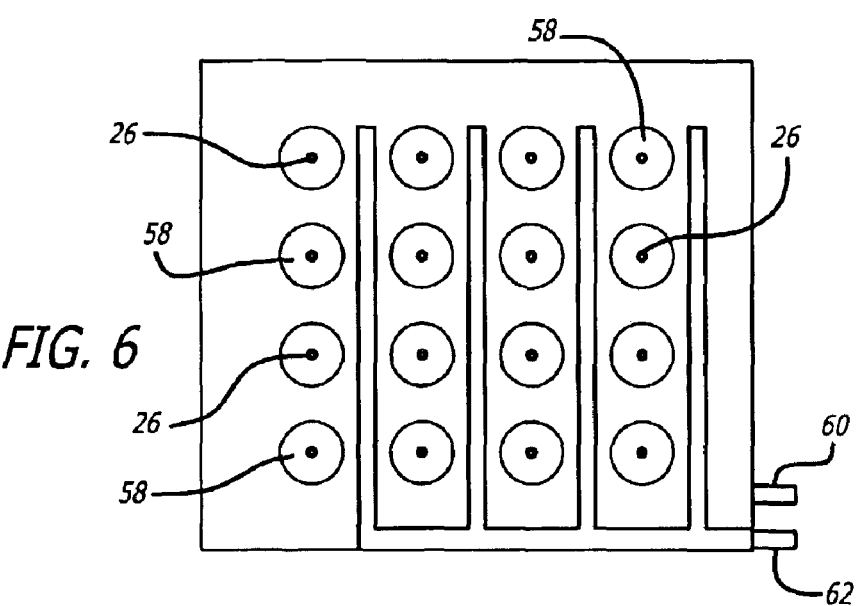
FIG. 6 is a plan bottom view of a multiple needle device.

In FIG. 6 there are shown multiple needles 26 which are arranged in a rectilinear fashion. There is the suction port 60 and suction port 62 located at one end of the relatively square profile of the housing for the device. As illustrated in FIG. 6 the system appears as a 16-cell system. The operation can be that each one of the needles 26 operates sequentially as required. The system is useful for drug delivery and replacement of different plasma and blood components in angiogenesis and in cell transplant technology, namely myogenesis.

As shown in FIG. 7 there is an arrangement without suction and where the tissue interface 38 is slightly spaced from the tips of the needles. When suction is applied to the port 60, the tissue 38 is drawn towards the interface at the end of the device. There is a connection with an OPVAC unit and the needle tips descend and penetrate the tissue as shown in FIG. 8. When suction or pressure is applied through port 62 the drug is delivered through the OPVAC unit into the tissue. This is illustrated in FIG. 9 with the drug being shown as drops 124. When the suction is removed the needles retract and the OPVAC action is removed.

In another form of the invention there can be configurations where there are peripheral bladders 120 around the drug bladder 114 which act to stabilize the device. This ensures the effective operation between the needle plate 110 and the drug plate 116.

In yet other forms of the invention there can be a configuration with spring members between the needle plate 110 and a structure below the needle plate towards the interface at the engaging end of the device. One or more of the spring members assist in the recoil of the needle plate and the needle into the device after delivery of the drug.

As illustrated in FIG. 10 there is a configuration for use of the device with endocardial or intramycardial tissue. Such a device would operate with an OPVAC-DD. It may be used to deliver fluids or therapy prior to drug delivery or in lieu of drug delivery. The therapy may include the removal of tissue scar or allow space for drug or cellular delivery. It could also include removal of tissue by true cut needle or passage of an ablation device. The ablation device may be a microwave, radio frequency (rf), laser or cryotherapy device. The ablation device rf 124 as illustrated in FIG. 10 penetrates a bore 126. The proximal end 128 of the device 130 can be used for engagement of the tissue 132. When the appropriate suction is applied to port 134, the bladder 136 which is circumferentially located inside of the housing contracts appropriately and causes the tissue 132 to be sucked into the centralized portion of the aperture of the device and thereby forms an inset surface portion 138. Wherein stabilization of the tissue is achieved in this manner the oblation device can be inserted through the bore 126. Drugs can also be delivered through the port 140 which thereby enters the bore 126 as required. The bladder 142 surrounds the bore 126 and a suitable port 144 is activated to cause the bladders to inflate or deflate as required.

As illustrated in FIG. 11, there is shown a device that is used as a needle delivery system. This permits for automatic needle delivery without a self-sticking requirements. In some uses of the device as shown in the Figures, a peripheral self-stick arrangement may be provided circumferentially about the outer periphery at the interface 24 of the cutaneous material. Such material can assist in stabilization of the device against the cutaneous layer.

In FIG. 11 the needle penetrates skin during drug delivery. With this device and other devices of the invention, a smaller needle, such as a micro needle, can be used and this causes less pain. It can be easily removed and replaced or relocated as necessary. The device can incorporate several needles and/or sensors. It can be connected to an i-pump with vacuum capability. In FIG. 11 there is a porous material 150 and a needle port 152 centrally located in the porous material. The porous material is mounted inside a housing 154 which itself can be secured with tape or fastener 156 to the tissue. The porous material is connected with a suction port 158 which is connected to an i-pump. Above the porous material there are sensors 160 which themselves are connected to the i-pump. Above that there is a needle plate 162 which is connected to the inside of the housing through an elastic diaphragm 164.

There are spring-like devices 166 which space the needle plate 162 from the top plate 168 of the housing. One or more ventilation ports 170 are provided to the housing. A drug port 172 is provided for the delivery of drugs through the needle port 152 as necessary. The drug port is also connected to the i-pump, as are the sensors 160. The device operates with a programmable i-pump which activates suction in the suction port. The suction passes through porous material and draws tissue or skin into the tissue port. The suction draws the needle plate downwardly and then the needle enters the tissue and the needle plate activates the sensor. The sensor relates to the i-pump the condition in which drugs can be delivered. Suction is then stopped. The elastic diaphragm and the elastic elements retract the needle.

As shown in FIG. 12 there is a feature where the needle plate may be part of an array to deliver several needles and having sensors into tissue. As such several needles 26 can be arranged with sensors 200 at the proximal end of the needle. The needles are connected with the needle plate 202. The sensor in some cases may be the needle itself or may be incorporated into the needle. The sensors can measure blood glucose and an i-pump can deliver the appropriate insulin through the needle.

A system with porous material is shown in FIG. 13. The porous material may incorporate into microbial agents either on the surface or impregnated to gradually leach out during the life of the device. Suction might activate a leaching process to sterilize tissue. The second port in the porous material can provide for anti-microbial irrigation prior to activation of a suction port in the device. The two suction ports, as illustrated in FIG. 13 are namely the tissue suction port 204 and the needle suction port 206. The tissue suction port is for causing the tissue to be drawn into the device so it can be stabilized when the needle 26 interacts with the tissue. The needle suction facilitates movement of the needle and/or irrigation of the tissue. Multiple suction ports may be added as required As shown in FIG. 14 there is an arrangement where the needle 26 is configured essentially to enter the tissue substantially at right angles. The needle 26 is right-angularly connected with the needle plate 208. As shown in FIG. 15 the needle 26 is constructed to enter the tissue obliquely, for instance at 45°. The needle 26 is located with the needle plate 210 at about 45°. Various angulations as such may be fashioned as required.

As shown in FIG. 16 there are several needles 26 which may pass through different portions of the cutaneous interface 38 at different sites. The operation of each of the needles 26 can be electromagnetically controlled through magnets 212 mounted on, with or in relation to each needle plate 214. An electromagnetic element 216 is mounted in adjacency with the magnets 212 to effect operation. A suitable sensor 218 is mounted towards the tip of the needle. Any suitable releasable mechanisms such as an electric switch or micro-switches may be applicable During the suction process the electromagnetic units 216 are operative and can hold or repel the ferrous needle plates, and four are illustrated in FIG. 16 as appropriate. Only one needle may penetrate the tissue as required. A fourth needle as indicated can use the sensor. The advantage of multiple needles is their different locations of penetration of the site are possible. Multiple drug deliveries can be achieved. The sensor can be configured to regulate delivery. The sensor can operate with a releasing mechanism controlled by a microprocessor or i-pump.

A self-administering system with the device and method of the invention is particularly advantageous. This could be for emergency use, for instance for administering a shot for something like anthrax vaccine. A patient who is self-administering a drug or the like could be nervous and the skin could be shaking which would otherwise cause problems. The vacuum or suction stabilizes the tissue and this stabilizes the device relative to the tissue to prevent any sideways movement of the needle, which may otherwise damage the skin. It also assists in achieving a consistent depth of needle penetration to avoid damage to other body structures such as tendons, nerves and bones.

The device can be used by a surgeon or other medical professional on internal body structures as well, rather than just the surface skin of an individual or other animal.

In some prior art devices, compressed air is used to deliver medication through the skin. Suction is better than compressed air for this purpose in that the suction stabilizes the skin and the device. Also, for a single use device, suction is preferable because compressed air could cause the device to expand.

The structure that contains the tubes that communicate the suction from the suction port to the various chambers can be a solid porous structure similar to the porous lava rock that is seen in fish tanks to create bubbles of air.

In another form the device is constructed to be usable repetitively, such as for the injection of botox into a wrinkle. This can also involve the use of a drug metering system.

In other versions there is puncturing of discrete portions of the membranes in the device that needs to work repetitively. If necessary a system is provided for effective re-sealing of the punctures or a valve operated by a cam or electric switch may be used. In yet other systems, differentials in pressure, ideally the application of a suction or vacuum, can be applied to one side and then an opposite side to move a bladder or membrane in opposite directions as necessary. For instance, a suction is applied to one side, and then a suction is applied to the other side to move the needle back and forth.

In some embodiments at least the tip or lead area of the housing 22 is relatively clear or transparent material so that the physician can see the area of skin to be punctured by the needle. This would have application, for instance, in the botox treatment where the doctor wants to follow a wrinkle line.

The diameter of the device can be made very small, just slightly larger than the needle in the interior. The needle 26 is not necessarily located in the center of the device.

Different advantages of the invention include the characteristics of the ability to preload the device with a drug vaccine or the like. This minimizes time for administration. It also facilitates the correct amount of preloading of the material to be injected. The vacuum grasping of the skin to a portion of the device facilitates stability of the skin and tissue prior to and during the injection of the material. The needle 26 acts automatically to puncture the skin and penetration effected to the correct skin depth. The content of the device can be delivered by vacuum or pressure and the operation can be a single one-action process. This one-action process can be effected in the sequence indicated. After automatically activating the device to apply suction to stabilize the skin, the subsequent steps of injection and retraction can take place automatically. After use the needle retracts into the device. This increases the safety of the system.

Other advantages include the multiple simultaneous drug delivery, multiple simultaneous needle punctures, the simplified ability to access difficult body sites, and the ability to use an ultrafine needle since the tissue is stabilized.

The overall system can be used similarly to a manner of grasping a pencil or pen, and different gripping mechanisms can be provided on the exterior of the body. There can also be one or more color indicators on the device to indicate the condition of the device. For instance, one color can be provided to indicate the device has not been used, a second color can be shown to indicate the device is penetrating the skin, and the third color can be used to indicate the device has been used and has been retracted and can now be discarded. These colors can show through one or more windows provided on the exterior of the body holding the device.

The device is essentially contained in a syringe-type barrel and contains the multiple chambers, namely the suction chamber, ventilation chamber, drug-containing chamber, and tissue securing area.

Different mechanisms can be used to organize the exact sequence and operation of some the components of the device. For instance, although the spring mechanism is indicated in the preferred example to become operative only after delivery of the drug from the drug bladder there may be systems where the spring does become operative slightly before or even after a delay of delivery of the drug. In this case the exact configuration of some of the components and application of some of the suctions and/or pressure in the device can vary for preferred applications.

The signaling system to indicate usage of the device can be a color indicator as well as an audible indicator. The audible indicator could operate as a whistle-type effect, by providing an aperture with a suitable reed-type valve which will emit a sound when the suction or pressure is applied to the aperture.

Other characteristics of the invention can include the provision of one or more adhesives or sticking elements to facilitate the adherence of the leading end of the device to the skin or tissue. Such an adhesive can be provided around the peripheral area of the device.

In other systems of the device there can be multiple tissue receiving ports with needles located therein to provide a cell-type structure for the device. These tissue ports can be provided in a series of parallel locations in the device. The overall device cross-section can adopt any appropriate shape. As such, although the device may normally appear to be cylindrical when there is a single tissue port and retractable needle in a system. Where there are multiple tissue ports the overall device can have any other cross-sectional shape. The shape can, for instance, be square or elongated.

A common source for providing suction can be provided to each of the particular cells of the multiple system. After use of a first cell the suction can be applied to a second and subsequent cell as required. Different cells may operate sequentially for suitable activation of a trigger by the doctor or the patient. In some other forms of the invention one or more additional biasing systems may be provided in appropriate places to facilitate the smooth and timely action of the components that such smooth action could accelerate the operation of some component or delay the action of some component as the case may be.

In yet other forms of the invention there can be a system whereby the needle delivers injectable material into tissue at multiple different delayed times. There can be a system where there is an automatic needle delivery system in which the needle penetrates the skin only during delivery of the drug. In different situations small needles such as microneedles can be used and this has the advantage of less pain for the patient. The easy removal and placement of the device is facilitated by the system. There can also be a situation where several needles can be incorporated where the one drug is delivered multiple times. There can be different sensors provided for each of the needles and the needles can operate in sequence or simultaneously as required.

The pump for applying the injection can be programmable so that the needles can be operated sequentially. This programming can be effected by electronic and/or mechanical means. As required, various degrees of complexity can be provided for most sophisticated systems for implementing the invention in its multiple uses and/or in arrays where needles and sensors are to be used. The sensor can be associated with a suction pump, bladder or needle and there can be one or more measuring devices in the device, for sensing and measuring bodily conditions before, during and after application of injectable material to the body.

One or more anti-microbial agents can be provided to the device on appropriate surfaces or impregnated so as to facilitate hygienic use and sterilization of components and/ or the tissue prior, during and after application of the device.

One or more areas of porous material can be provided to the device. For instance, one porous material may be provided around the tissue suction portion and a second porous material may be provided around the area relating to the needle suction. An impermeable region may be provided between those two porous materials. This can regulate the effect of the applied suction on the different components of the device.

In yet other forms of the invention the needle can be directed in a substantially longitudinal direction with the overall longitudinal shape of the device there can be situations where the needle is orientated at an angle which is non-longitudinal relative to the device. There can also be situations where there are multiple needles arranged around the area which stabilizes the tissue, and each of these needles can be directed at different angles relative to the device. We can penetrate the tissue at the appropriate angle with the tissue is stabilized in the tissue port. One or more release mechanisms can be used with each of the respective needles. Such release mechanisms can be magnetic or electromagnetic. This may be require operation of the electromagnetic systems which can operate with a delay or in a regulated programmable fashion relative to the application of the suction process for securing the tissue in the tissue port.

While the specification describes particular embodiments of the present invention, those of ordinary skill can devise variations of the present invention without departing from the inventive concept. The scope of the invention is to be determined by the following claims.

I claim:

1. A device for delivery of a fluid cutaneously comprising:
   a) a housing having a peripheral edge;
   b) a needle in the housing for piercing a cutaneous layer;
   c) a bladder for containing fluid for injection below the cutaneous layer;
   d) an area transversely within the peripheral edge of the housing and through which the proximal end of the needle may be directed, and the area being for receiving the surface of the cutaneous layer about which the proximal end of the needle is to pierce to effect an injection of fluid; and
   e) a suction generator for creating a suction force at the area thereby to urge the cutaneous layer towards the area within the peripheral edge of the housing and thereby provide a stabilizing force to the cutaneous layer;
   f) the arrangement of the needle, bladder and suction generator being such that the needle is caused to move by the suction force through the transverse area and thereby pierce the surface of the cutaneous layer; and permitting the expulsion of fluid from the bladder into the distal end of the needle and thereby permit the expulsion of fluid through the proximal end of the needle.

2. A device as claimed in claim 1 including a mounting for supporting a needle, and wherein a differential pressure causes the needle to move through the transverse area and provides a force to cause the movement of the needle mounting and thereby cause the needle to move between a position of repose relatively withdrawn from the transverse area and a position extending through the transverse area.

3. A device as claimed in claim 1 including permitting the bladder to move under a suction force towards the proximal end of the needle, and thereby permit the distal end to pierce the bladder and permit fluid from the bladder to enter the distal end of the needle and subsequently exit the proximal end of the needle.

4. A device as claimed in claim 1 wherein the bladder is formed in part of elastomeric material whereby the elastomeric material retains a force on the fluid in the bladder.

5. A device as claimed in claim 2 including applying a further suction to the needle mounting means and thereby permit movement of the plate a predetermined amount and thereby permit piercing of a sealed chamber in the housing, and thereby to cause venting of that suction force causing the needle to be urged from the position of repose.

6. A device as claimed in claim 1 including a biasing force for causing the needle to be normally urged from the transverse area.

7. A device as claimed in claim 1 including a surface on the transverse area, the surface being for receiving the cutaneous layer under action of the suction force, and thereby stabilizes the cutaneous layer prior to and during piercing of the cutaneous layer by the proximal end of the needle.

8. A device as claimed in claim 7 wherein the surface includes multiple ports through which a suction can be applied to the surface.

9. A device as claimed in claim 1 wherein there are multiple needles in relative adjacency with each other thereby to permit multiple piercings of the cutaneous layer.

10. A device as claimed in claim 1 including a suction generating chamber, an inlet from the suction generating chamber into the housing for transmitting the suction to the housing, at least one secondary needle for permitting a pressure connection between the inlet for the suction and a ventilation chamber after a predetermined amount of movement of the needle whereby the suction force is vented to the ventilation chamber.

11. A device as claimed in claim 10 wherein the venting of the suction force firstly permits the needle to be retracted from the exposed position, and thereafter permits the cutaneous layer to move from the transverse area.

12. A device as claimed in claim 1 wherein the housing is a cylindrical member with a circular outer edge, the transverse area being inwardly concavely shaped area within the peripheral outer edge to permit the cutaneous surface to be drawn under suction to form a convex shape against the concave surface, the concave surface having multiple outlets surrounding a location for permitting passage of the needle through the area.

13. A device as claimed in claim 1 including a ventilation chamber removed from the transverse area, there being a needle mounting means between the transverse area and the bladder being located between the needle mounting means and the ventilation chamber.

14. A device as claimed in claim 1 including signaling element for indicating the substantial completion of fluid expulsion from the needle, the signaling element selectively being an audible signal, the signal being caused by the suction.

15. A device as claimed in claim 1 wherein the needle is mounted with a movable plate, the plate having a biasing located between a block for holding the needle and the plate, the biasing acting to urge the block and needle from the plate, and the suction acting to urge the block towards the needle plate.

16. A device as claimed in claim 15 wherein the plate is mounted about its periphery with an internal wall of the housing, and wherein the mounting includes an elastic diaphragm thereby to permit movement of the plate under action of the biasing and the suction.

17. A device as claimed in claim 1 wherein the bladder is formed with a mounting plate for the needle, and wherein one wall of the bladder is the mounting plate, and wherein there is pierceable member of the mounting plate, such that, under suction, the plate is drawn towards the distal end of the needle, and the distal end of the needle is permitted to penetrate the pierceable member and enter the bladder.

18. A device as claimed in claim 1 wherein there is a normally sealed wall between the bladder and a ventilation chamber, and the suction beyond a predetermined level causes the breakage of the sealed wall and thereby the venting of the suction from the transverse area.

19. A device as claimed in claim 1 wherein the housing is an elongated structure, the needle being centrally located, and there being sequentially from a proximal end of the housing, firstly the transverse area including a surface through which the needle is adapted to move in an axial direction, a stabilizing block, one end of which forms the transverse surface, ports being directed through the block from a side removed from the transverse surface, a guide block for receiving a needle block so that the needle block is movable in the guide block, the guide block having ports to permit suction to pass to an axially movable needle mounting plate, and the suction inlet to the housing, the suction inlet being located between the guide block and the stabilizing block, a bladder connected with the needle mounting plate, and a ventilation chamber located on the opposite side of the bladder.

20. A device as claimed in claim 19 including a secondary needle to permit suction to pass from the suction inlet to the ventilation chamber when the needle plate is moved to a pre-selected position sufficiently close to the proximal end of the housing, and there being biasing for urging the needle plate to a position removed from the proximal end of the housing.

21. A device for delivery of a fluid cutaneously comprising:
   a) a housing having a peripheral edge;
   b) a needle in the housing for piercing a cutaneous layer;
   c) a bladder for containing fluid for injection below the cutaneous layer;
   d) an area transversely within peripheral edge of the housing and through which a proximal end of the needle may be directed, and the area being for receiving the surface of the cutaneous layer about which the proximal end of the needle is to pierce to effect an injection of fluid;
   e) means for generating a suction force at the area thereby to urge the cutaneous layer towards the area within the peripheral edge of the housing and thereby provide a stabilizing force to the cutaneous layer, the suction force causing the needle to move through the transverse area and thereby pierce the surface of the cutaneous layer, the suction force permitting the expulsion of fluid from the bladder into a distal end of the needle and thereby permit the expulsion of fluid through a proximal end of the needle;
   f) mounting means for supporting a needle, and wherein the suction force causes movement of the mounting means, thereby causing the needle to move between a position of repose relatively withdrawn from the transverse area and a position extending through the transverse area the suction force permitting the bladder to move towards the proximal end of the needle, and thereby permit the distal end to pierce the bladder and permit fluid from the bladder to enter the distal end of the needle and subsequently exit the proximal end of the needle; and
   g) the bladder being formed in part of elastomeric material whereby the elastomeric material retains a force on the fluid in the bladder.

22. A device as claimed in claim 21 including means for applying a further suction to the needle mounting means and thereby permit movement of the plate a predetermined amount and thereby permit piercing of a sealed chamber in the housing, and thereby to cause venting of that suction force causing the needle to be urged from the position of repose.

23. A device as claimed in claim 21 including a biasing means for causing the needle to be normally urged from the transverse area.

24. A device as claimed in claim 21 including a surface on the transverse area, the surface being for receiving the cutaneous layer under action of the suction force, and thereby stabilizes the cutaneous layer prior to and during piercing of the cutaneous layer by the proximal end of the needle.

25. A device as claimed in claim 21 wherein there are multiple needles in relative adjacency with each other thereby to permit multiple piercings of the cutaneous layer.

26. A device as claimed in claim 21 including a suction generating chamber, an inlet from the suction generating chamber into the housing for transmitting the suction to the housing, at least one secondary needle for permitting a pressure connection between the inlet for the suction and a ventilation chamber after a predetermined amount of movement of the needle whereby the suction force is vented to the ventilation chamber.

27. A device as claimed in claim 21 wherein the housing is a cylindrical member with a circular outer edge, the transverse area being inwardly concavely shaped area within the peripheral outer edge to permit the cutaneous surface to be drawn under suction to form a convex shape against the concave surface, the concave surface having multiple outlets surrounding a location for permitting passage of the needle through the area.

28. A device as claimed in claim 21 including a ventilation chamber removed from the transverse area, wherein said mounting means is between the transverse area and the bladder, the bladder being located between the mounting means and the ventilation chamber.

29. A device as claimed in claim 21 including signaling means for indicating the substantial completion of fluid expulsion from the needle, the signaling means selectively being an audible signal, the signal being caused by the suction.

30. A device as claimed in claim 21 wherein the needle is mounted with a movable plate, the plate having a biasing means located between a block for holding the needle and the plate, the biasing means acting to urge the block and needle from the plate, and the suction acting to urge the block towards the needle plate.

31. A device as claimed in claim 21 wherein the bladder is formed with a mounting plate for the needle, and wherein one wall of the bladder is the mounting plate, and wherein there is pierceable member of the mounting plate, such that, under suction, the plate is drawn towards the distal end of the needle, and the distal end of the needle is permitted to penetrate the pierceable member and enter the bladder.

32. A device as claimed in claim 21 wherein there is a normally sealed wall between the bladder and a ventilation chamber, and the suction beyond a predetermined level causes the breakage of the sealed wall and thereby the venting of the suction from the transverse area.

33. A device as claimed in claim 21 wherein the housing is an elongated structure, the needle being centrally located, and there being sequentially from a proximal end of the housing, firstly the transverse area including a surface through which the needle is adapted to move in an axial direction, a stabilizing block, one end of which forms the transverse surface, ports being directed through the block from a side removed from the transverse surface, a guide block for receiving a needle block so that the needle block is movable in the guide block, the guide block having ports to permit suction to pass to an axially movable needle mounting plate, and the suction inlet to the housing, the suction inlet being located between the guide block and the stabilizing block, a bladder connected with the needle mounting plate, and a ventilation chamber located on the opposite side of the bladder.

34. A method for delivery of a fluid cutaneously comprising:
   a) generating a suction force on a surface of a housing thereby to receive under the suction force a surface of a cutaneous layer about which the proximal end of a needle is to pierce to effect an injection of fluid;
   b) generating a suction force to operate the movement of a needle in the housing;
   c) moving a needle under the suction force from the housing thereby to permit piercing a cutaneous layer; and d) emptying a bladder for containing fluid into the distal end of the needle and thereby permit the expulsion of fluid through the proximal end of the needle for injection below the cutaneous layer.

35. A method as claimed in claim 34 including causing the needle to move through the transverse area under a suction force to cause the movement of the needle to move between a position of repose relatively withdrawn from the transverse area and a position extending through the transverse area.

36. A method as claimed in claim 34 including permitting the bladder to move under a suction force towards the proximal end of the needle, and thereby permit the distal end to pierce the bladder and permit fluid from the bladder to enter the distal end of the needle and subsequently exit the proximal end of the needle.

37. A method as claimed in claim 34 including applying a further suction to the needle and thereby permit a predetermined amount of movement and thereby permit piercing of a sealed chamber in the housing, and thereby to cause venting of that suction force causing the needle to be urged from the position of repose.

38. A method as claimed in claim 34 including biasing the needle to be urged from the transverse area, the biasing effect being operable selectively after the needle has been urged into he cutaneous region for a predetermined distance, and further selectively after the bladder has been substantially emptied.

39. A method as claimed in claim 34 including applying the suction force at multiple points on the surface thereby to stabilize the cutaneous layer.

40. A method as claimed in claim 34 including effecting multiple piercings of the cutaneous layer by multiple needles in the housing.

41. A method as claimed in claim 34 including transmitting the suction in the housing through at least one secondary needle for permitting a pressure connection between an inlet for the suction to be ventilated after a predetermined amount of movement of the needle.

42. A method as claimed in claim 41 wherein the venting of the suction force firstly permits the needle to be retracted from the exposed position, and thereafter permits the cutaneous layer to move from the transverse area.

43. A method as claimed in claim 34 including signaling the substantial completion of fluid expulsion from the needle, the signaling selectively being an audible signal, the signal being caused by the suction.

44. A method as claimed in claim 34 including moving the needle through a mounting with a movable plate, the plate being biased to urge the needle from the plate, and the suction acting to urge the needle towards the proximal end of the housing.

45. A method as claimed in claim 34 including piercing the bladder when the plate is drawn towards the distal end of the needle, and the distal end of the needle is permitted to penetrate and enter the bladder.

46. A method as claimed in claim 34 wherein the suction beyond a predetermined level causes venting of the suction from the transverse area.

47. A method for delivery of a fluid cutaneously comprising:

a) generating a suction force on a surface of a housing thereby to receive under the suction force a surface of a cutaneous layer about which the proximal end of a needle is to pierce to effect an injection of fluid;

b) generating a suction force to operate the movement of a needle in the housing;

c) moving a needle under the suction force from the housing thereby to permit piercing a cutaneous layer;

d) emptying a bladder for containing fluid into the distal end of the needle and thereby permit the expulsion of fluid through the proximal end of the needle for injection below the cutaneous layer;

e) moving the needle to move through the transverse area under a suction force and thereby cause the needle to move between a position of repose relatively withdrawn from the transverse area and a position extending through the transverse area; and f) moving the bladder to move under a suction force towards the proximal end of the needle, and thereby permit the distal end to pierce the bladder and permit fluid from the bladder to enter the distal end of the needle and subsequently exit the proximal end of the needle.

48. A method as claimed in claim 47 including applying a further suction to the needle and thereby permit movement a predetermined amount and thereby cause venting of that suction force causing the needle to be urged from the position of repose.

49. A method as claimed in claim 47 including biasing the needle to be urged from the transverse area, the biasing effect being operable selectively after the needle has been urged into he cutaneous region for a predetermined distance, and further selectively after the bladder has been substantially emptied.

50. A method as claimed in claim 47 including effecting multiple piercings of the cutaneous layer through multiple needles in the housing.

51. A device as claimed in claim 21 including means for venting suction after a predetermined amount of movement of the needle.

52. A device for delivery of a fluid cutaneously comprising:

a) a housing having a peripheral edge;

b) a needle in the housing for piercing a cutaneous layer;

c) a bladder for containing fluid for injection below the cutaneous layer;

d) an area transversely within the peripheral edge of the housing and through which the proximal end of the needle may be directed, and the area being for receiving the surface of the cutaneous layer about which the proximal end of the needle is to pierce to effect an injection of fluid; and e) a generator for creating a pressure differential, selectively a higher pressure force, or a suction pressure, and means to transmit the pressure differential as a suction at the area thereby to urge the cutaneous layer towards the area within the peripheral edge of the housing and thereby provide a stabilizing force to the cutaneous layer;

f) the arrangement of the needle, bladder and generator being such that the needle is caused to move by the pressure differential, selectively higher pressure force or the suction pressure through the transverse area and thereby pierce the surface of the cutaneous layer; and permitting the expulsion of fluid from the bladder into the distal end of the needle and thereby permit the expulsion of fluid through the proximal end of the needle.

* * * * *